(12) United States Patent
Beaumer et al.

(10) Patent No.: US 9,402,798 B2
(45) Date of Patent: Aug. 2, 2016

(54) CARRAGEENAN MIXTURES USEFUL AS COSMETIC INGREDIENTS AND HAIR STYLING GELS COMPRISING THEM

(75) Inventors: Christel Beaumer, Carentan (FR); Gertrudis Maria Juliaan Haest, Tienen (BE); Claudine Lefrancois, Appeville (FR)

(73) Assignee: Cargill, Incorporated, Wayzata, MN (US)

(*) Notice: Subject to any disclaimer, the term of this patent is extended or adjusted under 35 U.S.C. 154(b) by 0 days.

(21) Appl. No.: 13/497,143

(22) PCT Filed: Sep. 21, 2010

(86) PCT No.: PCT/EP2010/005756
§ 371 (c)(1),
(2), (4) Date: Mar. 20, 2012

(87) PCT Pub. No.: WO2011/032728
PCT Pub. Date: Mar. 24, 2011

(65) Prior Publication Data
US 2012/0183484 A1    Jul. 19, 2012

(30) Foreign Application Priority Data
Sep. 21, 2009 (EP) .................................... 09011979

(51) Int. Cl.
*A61K 8/73* (2006.01)
*A61Q 5/06* (2006.01)
*A61K 8/04* (2006.01)
*A61K 8/34* (2006.01)

(52) U.S. Cl.
CPC . *A61K 8/73* (2013.01); *A61K 8/042* (2013.01); *A61K 8/345* (2013.01); *A61Q 5/06* (2013.01)

(58) Field of Classification Search
CPC ......... A61K 8/042; A61K 8/345; A61K 8/73; A61Q 5/06
USPC ........................................ 424/70.13
See application file for complete search history.

(56) References Cited

U.S. PATENT DOCUMENTS

| | | | |
|---|---|---|---|
| 5,002,934 A * | 3/1991 | Norton et al. .................. 514/54 |
| 5,384,118 A | 1/1995 | LaValle |
| 5,972,356 A * | 10/1999 | Peffly et al. .................... 424/401 |
| 6,673,371 B2 * | 1/2004 | Brown et al. .................. 424/486 |
| 2003/0108607 A1 * | 6/2003 | Szymczak ...................... 424/479 |
| 2008/0031841 A1 * | 2/2008 | Laurent et al. .............. 424/70.11 |
| 2008/0039424 A1 * | 2/2008 | Restle et al. ................... 514/54 |
| 2008/0089855 A1 * | 4/2008 | Walter et al. ............... 424/70.11 |

FOREIGN PATENT DOCUMENTS

| | | |
|---|---|---|
| EP | 0445659 | 9/1991 |
| EP | 1884261 | 2/2008 |
| WO | WO 2011/032728 A1 | 3/2011 |

OTHER PUBLICATIONS

Elsevier et al.; "Light scattering studies of the dilute solution behavior of kappa-, iota-, and lamba-carrageenan", Food Hydrocolloids; 1996, vol. 10, No. 1 pp. 99-107.
PCT International Search Report PCT/EP2010/005756. Mailed Dec. 9, 2010. 3 Pages.

\* cited by examiner

*Primary Examiner* — Anoop Singh
*Assistant Examiner* — Doan Phan

(57) ABSTRACT

This invention provides a carrageenan mixture comprising about 60% to about 95% by weight of iota-carrageenans and about 5% to about 25% by weight of lambda-carrageenans, which is useful as an ingredient of a cosmetic formulation such as a fully natural hair styling gel being free from synthetic polymers.

4 Claims, No Drawings

CARRAGEENAN MIXTURES USEFUL AS COSMETIC INGREDIENTS AND HAIR STYLING GELS COMPRISING THEM

CROSS-REFERENCE TO RELATED APPLICATIONS

This application claims benefit of international application PCT/EP2010/005756, filed Sep. 21, 2010, which application claims priority to European Application 09011979.3, filed Sep. 21, 2009, which applications are hereby incorporated by reference herein in their entirety.

The present invention relates to carrageenan mixtures with specific characteristics which are useful as cosmetic ingredients for manufacturing cosmetic formulations, in particular for hair treatment. The present invention relates to entirely natural hair styling gels comprising such carrageenan mixtures, as well as to a process for manufacturing such hair styling gels.

BACKGROUND OF THE INVENTION

Several prior art references have already taught hair styling compositions including one or more carrageenans as an ingredient.

For instance, U.S. Pat. No. 6,132,704 discloses a hair styling gel composition comprising (a) a carboxylated polyurethane, (b) a viscosity enhancer, (c) a carrier comprising water, and (d) optionally up to 6% by weight of a second hair fixative resin which can be sodium carrageenan. This aqueous formulation can also contain up to 2% by weight of a conventional hair care adjuvant such as glycerine. No hint is given as to the specific type of carrageenan optionally used.

U.S. Patent Application Publication No. 2008/279,804 discloses a hair styling composition which binds to the hair surface due to charge and ion interaction and which comprises (a) 0.05 to 5% by weight of sodium magnesium silicate, (b) 0.05 to 1.5% by weight of a preservative, (c) optionally a thickener which can be a carrageenan in an amount of up to 5% by weight of the composition, and (d) water forming the balance. No hint is given as to the specific type of carrageenan optionally used. When the hair styling composition is a shampoo or a spray, it may further comprise up to 15% by weight of a humectant such as glycerin.

U.S. Patent Application Publication No. 2005/137272 discloses aqueous dispersions comprising:
(a) a gel forming polymer which may be a carrageenan,
(b) a gelling agent comprising a divalent, preferably calcium, cation capable of forming a gel at a pH of 3 or higher,
(c) a water soluble plasticizer such as glycerin,
(d) a pH modifier, e.g. a lactone, typically lowering the pH of the aqueous dispersion during gel formation, and
(e) water,
wherein the plasticizer comprises more than 50% by weight of the dry gel.

U.S. Pat. No. 6,623,727 discloses a solid gel composition for hair treatment comprising, in an aqueous or aqueous-alcoholic base (wherein the alcohol, e.g. glycerol, may be present at a content up to 40%), a combination of (a) 0.5 to 5% by weight of a carrageenan or mixture of carrageenans optionally admixed with a sugar such as dextrose and (b) at least one additive selected from the group consisting of hair fixing polymers, amphiphilic associative thickeners, salts containing calcium or potassium ions, mono-alcohols and polyalcohols. Kappa-carrageenan and iota-carrageenan are both suitable as component (a) of this gel composition. If the gel-former or the additive are not completely soluble at room temperature, heat can be used to dissolve them e.g. at about 40-80° C., then the resulting solution is allowed to stand until it solidifies to form the gel.

WO 2006/042588 discloses a hair styling product containing a foamable or sprayable, gel-type emulsion, in combination with a device for spraying or foaming the emulsion, said emulsion comprising (a) at least an ester of a polyalkoxylated polydimethylsiloxane, (b) at least an emulsifier, (c) water, and (d) at least a thickener which can be a carrageenan, in particular kappa-carrageenan and/or iota carrageenan, in an amount from 0.1 to 10% by weight.

U.S. Pat. No. 6,719,967 and U.S. Pat. No. 6,673,371 both disclose a hair treatment composition having a thickened fluid form and comprising:
(i) a first phase comprising a naturally derived polymer capable of forming a reversible gel, e.g. a carrageenan, and being present as a shear gel having multiple separate gel particles formed by subjecting the polymer to shear while gel formation occurs, and
(ii) a second phase suspended therein, being selected from the group of conditioning agents, solid active agents (e.g. antimicrobials, dyes or colorants), opacifying agents and pearlescing agents.

This composition displays a viscosity in the range of 0.1 Pa·s to 1000 Pa·s at a shear rate of 10 sec$^{-1}$ measured at 20° C. This composition may further comprise preservatives, or glycerine, at a level of up to 5% by weight. When the composition is formulated as a hair styling gel, it further comprises a water-soluble film-forming resin being a synthetic polymer. U.S. Pat. No. 6,719,967 and U.S. Pat. No. 6,673,371 also teach that:
other types of carrageenan may be used in mixtures with kappa carrageenan, and
aqueous solutions of iota carrageenan exist as reversible gels, but appear to be self-healing; therefore iota carrageenan can be used, but the resulting compositions become lumpy during storage because of the self-healing property of iota carrageenan gels.

The hair styling compositions of the prior art which include one or more carrageenans as an ingredient usually also include one or more synthetic polymers for performing functions such as, but not limited to, hair fixation. They can therefore be qualified as synthetic gels.

For obvious environmental reasons, one problem addressed by the present invention is the design of an entirely natural hair styling gel composition, i.e. a hair styling gel which is free from synthetic polymers but still performs the hair styling function, in particular the hair stiffening effect, in the same way as a synthetic gel.

Another problem addressed by the present invention is the development of a specific mixture of seaweed extracts which can be used as a cosmetic ingredient and which can avoid the need for synthetic polymers in making efficient cosmetic formulations such as, but not limited to, hair styling products.

The basic structure of carrageenans is a linear polysaccharide made up of a repeating dissacharide sequence of β-D-galactopyranose linked through positions 1,3 (A residues) and α-D-galactopyranose residues linked through positions 1,4 (B residues). The regular backbone structure of the basic structure of carrageenans is disrupted by a more or less ordered distribution of sulphate groups. Some of the galactose units have attached sulfate groups, while others are unsulfated. The three main types (iota, kappa and lambda) of carrageenan molecules differ by (1) the types of linkages between the galactose units, and (2) the point of attachment of the sulfate groups to the galactose units. These apparently small differences in chemical constitution and structure make major differences in the properties of each type of molecule.

Gelling in carrageenan is caused by helix formation and this can only occur in repeat structures where the B residue is in a 1-C-4 conformation. Lambda carrageenan (theoretically having 3 sulphate groups per repeating unit) has both its sugar residues in a 4-C-1 conformation and therefore does not form gels. It is therefore known to the skilled person that lambda carrageenan should be avoided when gelling is a strong requirement of the end use of a formulation including carrageenans.

All the gelling types of carrageenan which include the kappa type (theoretically having 1 sulphate group per repeating unit; the most naturally abundant type of carrageenan molecule) and the iota type (theoretically having 2 sulphate groups per repeating unit; the least naturally abundant type of carrageenan molecule) all contain a 3,6-anhydro bridge on the B unit which forces the sugar to flip from a 4-C-1 conformation to a 1-C-4 conformation and can then form cross-link networks and gels. However, kappa carrageenans may be prevented from gelling by the addition of sodium salts to the gum solution.

Some types of seaweed species contains relatively pure carrageenan fractions. *Kappaphycus Alvarezii* contains largely κ carrageenan and μ carrageenan which may be converted to kappa carrageenan by alkali treatment. *Eucheuma Denticulatum* contains a similarly high level of ι carrageenan with some ν carrageenan precursor. Other seaweeds are more mixed in their carrageenan content. *Furcellaran* contains a strong gelling type carrageenan which is a mix of kappa carrageenan and β carrageenan in a roughly 3:2 ratio. Other seaweed types, such as *Chondrus crispus* and *Gigartina* types contain not only a mix of κ and λ type carrageenans but also a type of carrageenan polymer that is essentially a block copolymer of different carrageenan types. This gives the carrageenan made from *Gigartina* or *Chondrus* weed species quite different properties from those made from the *Eucheuma* type species from South east Asia.

SUMMARY OF THE INVENTION

The present invention is based on a first unexpected finding that a significant proportion, i.e. from 5 to 25% by weight, of lambda-carrageenans in a carrageenan mixture based on a majority of iota-carrageenans is still able to provide a suitable balance of desirable physico-chemical properties, in particular rheological and gelling properties in aqueous media within a wide range of temperatures, that can be used in cosmetic formulations such as, but not limited to, hair styling products.

The present invention is based on a second unexpected finding that a significant proportion, i.e. from 5 to 25% by weight, of lambda-carrageenans in a carrageenan mixture based on a majority of iota-carrageenans is suitable for making an aqueous hair-styling product, in particular an aqueous hair-styling gel, without a need for incorporating synthetic polymers in its formulation.

DETAILED DESCRIPTION OF THE INVENTION

Based on the general principles outlined herein-above, a first aspect of the present invention relates to a hair styling gel comprising, per 100 parts by weight of said gel:
  from about 10 to about 20 parts by weight of a plasticizer,
  from about 2 up to about 3 parts by weight of a carrageenan mixture,
  from about 0.1 to about 1.0 parts by weight of a preservative, and
  water forming the balance,
characterised in that said carrageenan mixture comprises about 60% to about 95% by weight of iota-carrageenans and about 5% to about 25% by weight of lambda-carrageenans, and wherein said hair styling gel is free from synthetic polymers.

The respective proportions of iota-carrageenans and lambda-carrageenans in the carrageenan mixture, and the absence of synthetic polymers in the hair styling gel are two important features of the present invention. The determination of the effective proportions of iota-carrageenans and lambda-carrageenans in the carrageenan mixture has been made on the basis of:
  the hair styling effect to be achieved, in particular the type of hair stiffness or stiff-feel to be obtained and the lasting effect thereof, and
  the easiness of handling of the hair styling gel by the end user, i.e. the spreadability on the hands and the distributability in the hair.

This determination of the effective proportions also has to take into account that the end user may be subjected, depending upon the climate and the presence or absence of air-cooling, to substantial temperature variations during the period of time where the gel is expected to exhibit the desired hair styling effect.

Based on the balance of these requirements, and the rheological characteristics associated therewith, it has been found that:
  the proportion of iota-carrageenans in the carrageenan mixture of the hair styling gel of the present invention should not be above about 95% by weight and not below about 60% by weight, and
  the proportion of lambda-carrageenans in the carrageenan mixture of the hair styling gel of the present invention should not be above about 25% by weight, and not below about 5% by weight,
to achieve the desired hair styling effect and easiness of handling within a relatively broad temperature range.

In a specific embodiment of the present invention, the proportion of iota-carrageenans in the carrageenan mixture of the hair styling gel is not above about 90% by weight. In another specific embodiment of the present invention, the proportion of iota-carrageenans in the carrageenan mixture of the hair styling gel is not below about 75% by weight.

In a specific embodiment of the present invention, the proportion of lambda-carrageenans in the carrageenan mixture of the hair styling gel is not above about 20% by weight. In another specific embodiment of the present invention, the proportion of iota-carrageenans in the carrageenan mixture of the hair styling gel is not below about 10% by weight.

The lambda-carrageenans being present in the carrageenan mixture of the hair styling gel of the present invention preferably originate from Gigartinaceae. This family of algae, according to standard taxonomy, belongs to the order Gigartinales and itself includes several genera such as, but not limited to, *Gigartina, Chondrus*, and *Iridaea*.

In a specific embodiment of the present invention, the lambda-carrageenans being present in the carrageenan mixture of the hair styling gel originate from the *Chondrus* genus of Gigartinaceae. More specifically, these lambda-carrageenans may originate from one or more of the following species (all of them being currently accepted taxonomically): *Chondrus canaliculatus, Chondrus crispus, Chondrus elatus,*

*Chondrus giganteus, Chondrus ocellatus, Chondrus pinnulatus, Chondrus uncialis, Chondrus verrucosus*, and *Chondrus yendoi*.

In another specific embodiment of the present invention, the lambda-carrageenans being present in the carrageenan mixture of the hair styling gel originate from the *Gigartina* genus of Gigartinaceae. More specifically, these lambda-carrageenans may originate from one or more of the following species (all of them being currently accepted taxonomically): *Gigartina angulata, Gigartina brachiata, Gigartina bracteata, Gigartina clavifera, Gigartina decipiens, Gigartina densa, Gigartina dilitata, Gigartina disticha, Gigartina divaricata, Gigartina fissa, Gigartina flabellata, Gigartina imperialis, Gigartina insignis, Gigartina laciniata, Gigartina laingii, Gigartina lanceata, Gigartina lessonii, Gigartina macrocarpa, Gigartina minima, Gigartina minuta, Gigartina muelleriana, Gigartina multidichomata, Gigartina obovata, Gigartina paitensis, Gigartina paxillata, Gigartina pinnata, Gigartina pistillata, Gigartina polycarpa, Gigartina recurva, Gigartina rubens, Gigartina runcinata, Gigartina sonderi, Gigartina tysonii*, and *Gigartina wehliae*.

In another specific embodiment of the present invention, the lambda-carrageenans being present in the carrageenan mixture of the hair styling gel originate from the *Iridaea* genus of Gigartinaceae. More specifically, these lambda-carrageenans may originate from one or more of the following species (all of them being currently accepted taxonomically): *Iridaea ciliata, Iridaea cordata, Iridaea lanceolata, Iridaea latissima, Iridaea mawsonii, Iridaea micrococca, Iridaea remuliformis, Iridaea tuberculosa*, and *Iridaea undulosa*.

The carrageenan mixture present in the hair styling gel of this invention may further optionally comprise very minor amounts of other carrageenans which are neither lambda-carrageenans nor iota-carrageenans. The presence of such other carrageenans may be due to the natural source of lambda-carrageenans or iota-carrageenans being used, and/or to the treatment conditions used to obtain relatively pure lambda-carrageenans or iota-carrageenans from natural sources. Such other carrageenans may have 3 sulphate groups per repeating unit (such as for instance nu-carrageenans) or 2 sulphate groups per repeating unit (such as for instance μ-carrageenans or theta-carrageenans) or 1 sulphate group per repeating unit (such as for instance theta-carrageenans). One important feature of this embodiment of the hair styling gel of this invention is that the proportion of such other carrageenans in the carrageenan mixture should be low enough to avoid any significant modification of the desired hair styling effect, easiness of handling of the hair styling gel, and rheological characteristics over the relevant temperature range. This means in practice that the proportion of such other carrageenans in the carrageenan mixture should be very minor, e.g. should not be above 15% by weight, preferably not above 10% by weight, more preferably not above 5% by weight. In practice, such very minor amounts of other carrageenans may simply correspond to the level of impurities which may be found in lambda-carrageenans or iota-carrageenans, depending upon the exact seaweed source and upon the conditions of alkaline treatment applied to that seaweed source.

According to another embodiment of the present invention, the carrageenan mixture present in the hair styling gel of this invention may comprise no other carrageenans than lambda-carrageenans or iota-carrageenans, i.e. the carrageenan mixture may consist of, or consist essentially of, about 75% to about 95% by weight of iota-carrageenans and about 5% to about 25% by weight of lambda-carrageenans. In a specific embodiment of the present invention, the carrageenan mixture may consist essentially of about 75% to about 90% by weight of iota-carrageenans and about 10% to about 25% by weight of lambda-carrageenans.

The proportion of plasticizer in the hair styling gel is another important feature of the present invention. The determination of the effective proportion of plasticizer has been made on the basis of the same balance of the gel efficiency and applicability requirements, and the rheological characteristics associated therewith, as the selection of respective proportions of iota-carrageenans and lambda-carrageenans in the carrageenan mixture. The proportion of plasticizer in the hair styling gel of the present invention should not be above about 20% by weight, preferably not above about 18% by weight. The proportion of plasticizer in the hair styling gel of the present invention should not be below about 10% by weight, preferably not below about 12% by weight. Preferred plasticizers include, but are not limited thereto, glycerin, sorbitol and mixtures thereof. In a highly preferred embodiment, the plasticizer is glycerin. In yet another highly preferred embodiment, the plasticizer is a combination of glycerin and sorbitol at a glycerin:sorbitol weight ratio of from 1.5:1 to 1:1.5, preferably from 1.2:1 to 1:1.2, even more preferably from 1.2:1 to 1:1.1. Although glycerin or sorbitol can easily be found in a high purity form, the presence of impurities as typically found in commercially available grades of these plasticizers, will normally not affect gel performance.

According to other embodiments of the present invention, one or more of the following specific features may be important for the hair styling gel components and/or its rheological behaviour within the relevant temperature range:
- the degree of sulfation of the iota-carrageenans present in the carrageenan mixture may be above about 25% (e.g. above 27%) or below about 35% (e.g. below 33%), such as within a range from about 25 to about 35%;
- the degree of sulfation of the lambda-carrageenans present in the carrageenan mixture may be above about 20% (e.g. above 22%) or below about 35% (e.g. below 33%), such as within a range from about 20 to about 35%;
- the average degree of sulfation of the carrageenan mixture may be above about 20% (e.g. above 22%) or below about 35% (e.g. below 33%), such as within a range from about 22 to about 35%;
- the viscosity of the hair styling gel may be above about 20 Pa·s (e.g. above about 30 Pa·s) or below about 70 Pa·s (e.g. below about 60 Pa·s), such as within a range from about 20 to about 70 Pa·s at a shear rate of 1 $s^{-1}$ measured at 20° C.;
- the viscosity of the hair styling gel may be above about 0.7 Pa·s (e.g. above about 1.0 Pa·s) or below about 2.0 Pa·s, such as within a range from about 0.7 to about 2.0 Pa·s at a shear rate of 200 $s^{-1}$ measured at 20° C.

The proportion of the preservative in the hair styling gel is another important feature of the present invention. Contrary to the teaching of U.S. Pat. No. 6,132,704, which does not consider the presence of a preservative, and of U.S. Pat. No. 6,623,727 that a preservative is not absolutely required when at least 15% by weight of an alcohol such as glycerol is used in a solid gel composition for hair treatment based on kappa-carrageenan, it has been found that a preservative is required for the hair styling gel of the present invention. The proportion of the preservative in the hair styling gel of the present invention should be at least 0.1% by weight, preferably at least 0.2% by weight. The proportion of the preservative in the hair styling gel of the present invention should be at most 1.0% by weight, preferably at most 0.5% by weight, even more preferably at most 0.4% by weight. Examples of suitable preservatives for incorporation into the hair styling gel of the present invention include, but are not limited to, non-polymeric preservatives for preventing microbial contamination and/or oxidation. Typical preservatives include, but are not limited to, diazolidinyl urea, iodopropenyl butylcarbamate, vitamin E (alpha-tocopherol), vitamin E acetate (alpha-tocopherol acetate), vitamin C (ascorbic acid), butylated hydroxytoluene, butylated hydroxyanisole, methylparaben, ethylparaben, n-propylparaben, dehydroacetic acid and mixtures thereof in any suitable proportions.

The hair styling gel of the present invention may further comprise one or more other non-polymeric ingredients conventionally used in hair treatment formulations such as, but not limited to, waterproofing agents, perfumes, colouring agents, plant extracts such as Aloe Vera, conditioners, antimicrobial agents, pH adjusters, chelating agents such as EDTA, sunscreens and fragrances. Each of these other optional ingredients will be present in an amount effective to accomplish its own purpose, e.g. an amount of up to about 5% by weight of the total composition. The hair styling gel compositions of this invention may also contain optional non-polymeric adjuvants suitable for hair care, e.g. in an amount of up to about 2% by weight of the total composition. Suitable hair care adjuvants include, but are not limited to, natural hair root nutrients such as one or more amino-acids. Examples of suitable amino acids include, but are not limited to, arginine, cysteine, glutamine, glutamic acid, isoleucine, leucine, methionine, serine, valine, and mixtures thereof in any proportions. These amino acids may be added singly, or in the form of oligopeptides, e.g. di- and/or tripeptides. For the purpose of the present invention, such oligopeptides shall not be regarded as polymeric substances. These amino acids may also be added in the form of a protein hydrolysate, such as a keratin or collagen hydrolysate.

In another specific embodiment, the hair styling gel composition of the present invention may be sugar-free.

The hair styling gel compositions of the present invention exhibit various significant advantages over the previously known compositions:

they are free from the synthetic polymers usually present for contributing to the hair styling effect, which makes them essentially natural compositions;

they are able to achieve the desired hair styling effect and easiness of handling within a relatively broad temperature range, e.g. at temperatures above about 15° C., preferably above about 20° C., and/or at temperatures below about 50° C., preferably below about 40° C., more preferably below 35° C., with the consequence that they can be applied and keep their hair styling effect not only under air conditioning inside a building but also in the outside under warm climatic conditions.

they have good transparency properties, which is an important requirement in today's hair styling gels.

In another specific embodiment, the hair styling gel composition of the present invention further comprises a flake reduction agent. Suitable flake reduction agents include, but are not limited to xanthan gum, ethanol, erythritol an combinations thereof. Xanthan gum is preferably present at a level of from about 0.05% to about 0.3% by weight of the composition, more preferably from about 0.05 to about 0.2%, even more preferably about 0.1%. Ethanol is preferably present at a level of from about 0.5% to about 5% by weight of the composition, more preferably from about 1% to about 4% by weight of the composition, more preferably about 3% by weight of the composition. Erythritol is preferably present at a level of from about 1% to about 6% by weight of the composition, more preferably from about 2% to about 5% by weight of the composition, even more preferably about 3% by weight of the composition. The problem of flake formation of hair styling gels is a well known problem, especially occurring when a hair styling gel is combed out of the hair. It has been surprisingly found that the addition of these flake reduction agent to the hair styling gel compositions significantly reduce, or even eliminate, flake formation.

A second aspect of the present invention relates to a process for making a hair styling gel as defined in the first aspect herein-above (including all specific embodiments thereof), characterised in that said process comprises at least the steps of:

(a) dispersing from 2 up to 3 parts by weight of a carrageenan mixture comprising from 60% to 95% by weight of iota-carrageenans and from 5% to 25% by weight of lambda-carrageenans into 10 to 20 parts by weight of plasticizer, (b) pouring water onto the dispersion obtained in step (a) and mixing the resulting aqueous dispersion, and (c) adding from 0.1 to 1.0 parts by weight of a preservative to the aqueous dispersion obtained in step (b).

The amount of water poured in step (b) is such that it forms the balance to 100 parts by weight of the gel composition.

An advantageous feature of the process of the present invention is that, due to the higher solubility of lamda carrageenans in cold water, each of steps (a), (b) and (c) may be performed at a temperature not above 25° C. (e.g. at 20° C.) and/or for a short period of time. In other words, contrary to the teaching of U.S. Pat. No. 6,623,727, there is no need to make use of heat or to wait until solidification to obtain the desired gel. According to a specific embodiment of the present invention, mixing in step (b) may be effected during at least about 5 minutes, or at least about 10 minutes. According to another specific embodiment of the present invention, mixing in step (b) may be effected during at most about 45 minutes, or at most about 30 minutes. Mixing in step (b) may be effected at moderate rotation speed or at high rotation speed, in a manner well known to those skilled in the art.

A third aspect of the present invention relates to a novel carrageenan mixture comprising (or consisting of, or consisting essentially of) 60% to 95% by weight, preferably from 75% to 90% by weight of iota-carrageenans with a degree of sulfation within a range from 25 to 35% and 5% to 25% by weight, preferably 10% to 25% by weight of lambda-carrageenans with a degree of sulfation within a range from 20 to 35%. Each more specific embodiment described herein-above in respect of the first aspect of the present invention, such as proportion, origin, and sulfation degree of a carrageenan component, is applicable here. The carrageenan mixture may further comprise a flake reduction agent as described hereinbefore.

A fourth aspect of the present invention relates to the use of the novel carrageenan mixture defined in the third aspect herein-above (including all specific embodiments thereof) as a cosmetic ingredient. The novel carrageenan mixture may be used as an ingredient in any type of cosmetic formulation wherein its specific rheological behaviour (e.g. viscosity at low and high shear rates) is desirable. Such cosmetic formulations are not limited to hair styling gels but also include other hair treatment formulations such as shampoos and conditioners, personal washing compositions and the like. Within the framework of the fourth aspect of the present invention, the novel carrageenan mixture may be combined with one or more ingredients for personal care and topical health care products. The latter typically include, but are not limited to, solvents (e.g. lower mono-alcohols having from 1 to 4 carbon atoms), surfactants (e.g. cleansing agents, emulsifying agents, foam boosters, hydrotropes, solubilizing agents, and suspending agents), non-surfactant suspending agents, emulsifiers, skin conditioning agents (emollients, moisturizers, and the like), hair conditioning agents, skin protecting agents, binders, chelating agents, antimicrobial agents, antifungal agents, antidandruff agents, abrasives, absorbents, colorants, deodorant agents, antiperspirant agents, humecting agents, opacifying agents and pearlescing agents, antioxidants, preservatives, propellants, spreading agents, sunscreen agents, sunless skin tanning accelerators, ultraviolet light absorbers, pH adjusting agents, hair colorants, oxidising agents, reducing agents, skin bleaching agents, pigments, physiologically active agents, anti-inflammatory agents, topical anaesthetics, fragrance and fragrance solubilizers, and the like.

A fifth aspect of the present invention relates to method of treating hair comprising the step of applying to hair a composition comprising a carrageenan mixture as defined in the third aspect herein-above (including all specific embodiments thereof), in particular a hair styling gel as defined in the first aspect herein-above (including all specific embodiments thereof). In one specific embodiment, this method provides the advantage of treating hair without contacting hair with potentially harming synthetic polymers.

The present invention is now illustrated by way of one working example evidencing its important features and resulting advantages.

EXAMPLE

First a carrageenan mixture comprising 85% by weight of iota-carrageenans extracted from *Euchema denticulatum* with a degree of sulfation of 30% and 15% by weight of lambda-carrageenans extracted from *Gigartina* with a degree of sulfation of 30% was prepared using an overhead stirrer.

Then a hair styling gel formulation was produced by performing the following steps:
- 2.6 parts by weight of the above carrageenan mixture was dispersed into 15 parts by weight glycerin under agitation,
- 82.1 parts by weight of distilled water was poured onto the carrageenan-glycerin dispersion and mixed at room temperature (20° C.) for 20 minutes, and
- 0.3 parts by weight of dehydroacetic acid acting as a preservative was finally added.

Rheological properties of the resulting hair styling gel formulation were measured by means of a Haake VT 550 rheometer equipment.

The rheological behaviour of the formulation was characterised at room temperature (20° C.) by its viscosity at both low and high shear rates:
53 Pa at 1 $s^{-1}$, and
1.7 Pa at 200 $s^{-1}$.

This hair styling gel formulation was found to provide a suitable hair styling effect within a temperature range from 15° C. to 35° C.

What is claimed is:

1. A hair styling gel comprising, per 100 parts by weight of gel:
   from about 12 to about 20 parts by weight of a plasticizer;
   from about 2 to about 3 parts by weight of a carrageenan mixture;
   form about 0.1 to about 1.0 parts by weight of a preservative; and
   water forming the balance,
   wherein the carrageenan mixture consists of iota-carrageenans and lambda-carrageenans;
   wherein the iota-carrageenans is about 60% to about 95% by weight of the carrageenan mixture and the lambda-carrageenans is about 10% to about 25% by weight of the carrageenan mixture;
   wherein the iota-carrageenans has a degree of sulfation within a range of about 25% to about 35% and the lambda-carrageenans has a degree of sulfation within a range of about 20% to about 35%;
   wherein the hair styling gel is free from synthetic polymers;
   wherein the hair styling gel has a viscosity from about 30 Pa·s to about 70 Pa·s at a shear rate of 1 $s^{-1}$ measured at 20° C.; and
   wherein the hair styling gel has a viscosity from about 0.7 Pa·s to about 2.0 Pa·s at a shear rate of 200 $s^{-1}$ measured at 20° C.

2. The hair styling gel of claim 1, wherein the lambda-carrageenans originate from Gigartinaceae.

3. The hair styling gel of claim 1, wherein the plasticizer is selected from the group consisting of glycerine, sorbitol, and mixtures thereof.

4. The hair styling gel of claim 1, wherein the hair styling gel further comprises a flake reduction agent, the flake reduction agent selected from the group consisting of xanthan gum, ethanol, erythritol, and combinations thereof.

* * * * *